United States Patent [19]
Rollins et al.

[11] Patent Number: 5,739,103
[45] Date of Patent: *Apr. 14, 1998

[54] CHEMOKINE N-TERMINAL DELETION MUTATIONS

[75] Inventors: Barrett Rollins; Yujun Zhang, both of Brookline, Mass.

[73] Assignee: Dana-Farber Cancer Institute, Boston, Mass.

[*] Notice: The term of this patent shall not extend beyond the expiration date of Pat. No. 5,459,128.

[21] Appl. No.: 455,629

[22] Filed: May 31, 1995

Related U.S. Application Data

[63] Continuation-in-part of Ser. No. 330,218, Oct. 27, 1994, Pat. No. 5,459,128, which is a continuation-in-part of Ser. No. 152,301, Nov. 12, 1993, abandoned.

[51] Int. Cl.$^6$ .................. C07K 14/52; C08H 1/00; A61K 38/19; A61K 45/05
[52] U.S. Cl. .................. 514/8; 424/85.1; 514/12; 514/21; 530/351; 530/395; 530/402; 530/409
[58] Field of Search .................. 530/350, 351, 530/395, 402, 409; 514/8, 12, 21; 424/85.1; 930/140, 141

[56] References Cited

U.S. PATENT DOCUMENTS 5,459,128  10/1995  Rollins et al. .................. 514/8

FOREIGN PATENT DOCUMENTS

| WO92/06112 | 4/1992 | WIPO. |
| WO92/19737 | 11/1992 | WIPO. |
| WO94/21277 | 9/1994 | WIPO. |
| WO94/29341 | 12/1994 | WIPO. |
| WO95/13295 | 5/1995 | WIPO. |

OTHER PUBLICATIONS

Zhang, Y. et al., "Structure/Activity Analysis of Human Monocyte Chemoattractant Protein–1 by Mutagenesis," *J. Biol. Chem.*, 269(22):15918–15924 (Jun. 3, 1994).

Moser, B. et al., "Interleukin–8 Antagonists Generated by N–Terminal Modification," *J. Biol. Chem.*, 268(10):7125–7128 (Apr. 1993).

Gong, J–H et al., "Antagonist of Monocyte Chemoattractant Protein–1 by Modification of the Functionally Critical N–terminal Residues," *J. Exp. Med.*, 181:631–640 (Feb. 1995).

Rollins, Barrett et al., "Recombinant Human MCP–1/JE Induces Chemotaxis, Calcium Flux and Respiratory Burst in Human Monocytes," *Blood*, 78(4):1112–1116 (1991).

Prickett, K.S. et al., "A Calcium–dependent Antibody for Identification and Purification of Recombinant Proteins," *Biotechniques*, 7(6):580–589 (1989).

Koch, A.E. et al., "Enhanced production of chemotactic cytokines interleukin–8 and monocyte chemoattractant protein–1 in human abdominal aortic aneurysms," *Am. J. Pathol.*, 142(s):1423–1431 (May 1993).

Schnitzel, Wolfgang et al., "Monomer–dimer equilibria of interleukin–8 and neutrophil–activating peptide 2. Evidence of IL–8 binding as a dimer and oligomer to IL–8 receptor B," *J. Leukocyte Biol.*, 55:763–770 (1994).

Clark–Lewis, Ian et al., "Structure–activity relationships of chemokines," *Journal of Leukocyte Biology*, 57(5):703–711 (1995).

Gong, Jiang–Hong et al., "RANTES and MCP–3 Antagonists Bind Multiple Chemokine Receptors," *Journal of Biological Chemistry*, 271(18):10521–10527 (1996).

Zhang, Yujun and Rollins, Barrett J., "A Dominant Negative Inhibitor Indicates that Monocyte Chemoattractant Protein 1 Functions as a Dimer," *Molecular and Cellular Biology*, 15(9):4851–4855 (1995).

*Primary Examiner*—Nancy Degen
*Attorney, Agent, or Firm*—Hamilton, Brook, Smith & Reynolds, P.C.

[57] ABSTRACT

The invention relates to mutant chemokines and pharmaceutical compositions thereof, wherein the mutant inhibits the corresponding endogenous chemokine from binding or activating a responsive receptor. The claimed mutant chemokines can be administered to a patient for the treatment or prophylaxis of a chemokine-mediated disease. The invention further relates to isolated DNAs encoding the mutant chemokines, vectors and recombinant host cells containing the same.

21 Claims, 9 Drawing Sheets

|  | anti-FLAG | | IgG |
|---|---|---|---|
| $^{125}$I-MCP-1 | + | + | + |
| $^{125}$I-RANTES |  | + | + | + |
| FLAG-MCP-1 | + | + |  | + | + |
| FLAG-7ND | — | — | + | + | — | — |

|  | anti-FLAG | | IgG |
|---|---|---|---|
| $^{125}$I-MCP-1 | + | + | + |
| $^{125}$I-IL-8 |  | + | + | + |
| FLAG-MCP-1 | + | + |  | + | + |
| FLAG-7ND | — | — | + | + | — | — |

|       |             | Specific Activity | |
|-------|-------------|-------|-------|
|       |             | U/mg  | %     |
| WT    |             | 442,000 | 100.0 |
| FX2   |             | 408,000 | 92.3  |
| FX3   |             | 1100 | 0.2   |
| 7ND   |             | 38    | 0.009 |
| D3A   |             | 40,000 | 9.0   |
| N6A   |             | 234,000 | 52.9  |
| R24F  |             | 22,300 | 5.0   |
| S27Q  |             | 265,000 | 60.0  |
| Y28D  |             | 1100  | 0.2   |
| R30L  |             | 19    | 0.004 |
| D1    |             | 50,000 | 11.3  |
| D2    |             | 75,000 | 17.0  |
| D68L  |             | 50,000 | 11.3  |

CHEMOKINE N-TERMINAL DELETION MUTATIONS

RELATED APPLICATION

This application is a continuation-in-part of Ser. No. 08/330,218 filed Oct. 27, 1994, now U.S. Pat. No. 5,459,128 which is a continuation-in-part under Rule 1.62 File Wrapper Continuing Application of Ser. No. 08/152,301, filed Nov. 12, 1993, now abandoned, the entire teachings of which are incorporated herein by reference.

GOVERNMENT SUPPORT

The invention described herein was supported in whole or in part by Grant No.: CA53091 from the National Institutes of Health. The Government has certain rights in the invention.

BACKGROUND OF THE INVENTION

Chemokines share a high degree of amino acid sequence similarity (Oppenheim, J. J. et al., *Annu. Rev. Immunol.* 9:617–648 (1991); Rollins, B. J., In Mertelsmann, R., and F. Herrmann (ed.), *Hematopoietic Growth Factors in Clinical Applications*, pg. 257–280, 2nd ed. Marcel Dekker, Inc., New York (1994); Schall, T. J., *Cytokine* 3:165–183 (1991)). Chemokines have 4 cysteines in conserved positions, but two subfamilies can be distinguished based on the absence or presence of an intervening amino acid between the two cysteines nearest the N-termini of the proteins. The former subfamily is denoted C—C and includes monocyte chemoattractant protein-1 (MCP-1), which is a potent chemoattractant for monocytes and T lymphocytes (Rollins, *Molecular and Cellular Biology*, 9(11):4687–4695 (1989); Carr, M. W. et al., *Proc. Natl. Acad. Sci. USA* 91:3653–3656 (1994); Matsushima, K., et al., *J. Exp. Med.* 169:1485–1490 (1989); Yoshimura, T. et al., *J. Exp. Med.* 169:1449–1459 (1989)) and induces histamine release from basophils (Bischoff, S. C. et al., *J. Exp. Med.* 125:1271–1275 (1992); Kuna, P. et al., *J. Exp. Med.* 175:489–493 (1992)). The latter subfamily is denoted C-X-C and includes the neutrophil chemoattractant, IL-8.

Solved chemokine structures, including those of IL-8, platelet factor 4 (PF4), MIP-1β and MCP-1, have been studied and the tertiary structures of these chemokine monomers are considerably similar. However, under conditions required for crystallization or NMR analysis, these chemokines form dimers, and despite the nearly identical structures of their monomeric subunits, the structures of the dimers differ appreciably. For example, the IL-8 dimer is compact (Baldwin, E. T. et al., *Proc. Natl. Acad. Sci. USA* 88:502–506 (1991) and Clore, G. M. et al., *Biochemistry* 29:1689–1696 (1990)), while the MIP-1β dimer (another C—C chemokine) is elongated and cylindrical (Lodi, P. J. et al., *Science* 263:1762–1767 (1994)). The structure of the MCP-1 dimer is similar to that of MIP-1β (Handel et al., *Chemotactic Cytokines*, IBC USA Conferences, Inc., Washington, D.C. (1994)).

Chemokines are proinflammatory cytokines that are chemoattractants and activators of specific types of leukocytes and have been identified as playing a significant role in many disease states.

Aberrant expression of MCP-1, for example, occurs in a variety of diseases that feature a monocyte-rich inflammatory component, such as atherosclerosis (Nelken, N. A. et al., *J. Clin. Invest.* 88:1121–1127 (1991); Yla-Herttuala, S. et al., *Proc. Natl. Acad. Sci. USA* 88:5252–5256 (1991)) and rheumatoid arthritis (Koch, A. E. et al., *J. Clin. Invest.* 90:772–779 (1992)). Rational design of chemokine inhibitors to treat these diseases depends on understanding how the chemokine interacts with its receptor, in the case of MCP-1, a seven-transmembrane spanning (7-TMS), G protein-coupled receptor (Charo, I. F. et al., *Proc. Natl. Acad. Sci. USA* 91:2752–2756 (1994)). A critical and contentious issue about chemokine:receptor interaction is whether the ligands bind to their receptors as dimers. Estimates for the affinity of chemokine dimerization place the $K_d$ for monomer association several logs above the $EC_{50}$ for biological activity and the $K_d$ for receptor binding (Paolini, J. F. et al., *J. Immunol.* 1531:2704–2717 (1994); Rajarathnam, K., et al., *Science* 264:90–92 (1994)). In addition, variant IL-8 proteins that are unable to dimerize in solution have full biological activity on neutrophils (Rajarathnam, K., et al., *Science* 264:90–92 (1994)).

Thus, there is a need to further elucidate the chemokine-receptor interaction and develop inhibitors to treat chemokine-mediated disease.

SUMMARY OF THE INVENTION

The invention relates to the surprising discovery that N-terminal deletions of chemokines are potent dominant negative inhibitors of chemokine-receptor interaction by forming heterodimers with the corresponding endogenous monomer of the chemokine. Thus, the invention relates to chemokine N-terminal deletion mutations, their use to form heterodimers with the corresponding endogenous chemokine monomer, in vivo or in vitro, and their use to treat chemokine-mediated diseases.

BRIEF DESCRIPTION OF THE DRAWINGS

FIG. 2A FX2 ($M_r$ 30,600); FIG. 2B 7ND ($M_r$ 15,500). FIG. 2C N-terminal FLAG epitope-tagged MCP-1 ($M_r$ 30,600). Molecular weight markers include bovine γ-globulin (γG, $M_r$ 158,000), chicken ovalbumin (Ova, $M_r$ 44,000), equine myoglobin (Mb, $M_r$ 17,000), and vitamin $B_{12}$ ($B_{12}$, $M_r$ 1350).

FIG. 3 illustrates crosslinked MCP1 tested in an in vitro monocyte chemoattraction assay. Molar concentrations were determined by assuming an average molecular weight based on the proportional contribution of each molecular species to the crosslinked preparation. Error bars indicate the standard error of measurements in duplicate wells; this experiment is representative of three.

DETAILED DESCRIPTION OF THE INVENTION

The invention relates to mutant chemokines comprising an N-terminal deletion mutation of the corresponding chemokine, wherein the mutant chemokine inhibits binding and/or activation of a chemokine receptor responsive to the corresponding, endogenous chemokine. The chemokine can be a C—C or a C—X—C chemokine. The chemokine can be, for example, MCP-1, MCP-2, MCP-3, MIP-1α, MIP-1β, RANTES, platelet factor 4, IP-10, GROα, GROβ, GROγ, NAP-2, ENA-78, CTAP-III, MIG and I-309. The mutant chemokine of the present invention does not include N-terminal deletion mutations of interleukin-8.

In a preferred embodiment, the N-terminal region, the chemokine conserved amino acids therein or a significant portion thereof is deleted, for example, amino acids between about 1 to about 13, about 1 to about 10 or about 2 to about 7 of the corresponding chemokine are deleted.

The mutant chemokine can additionally contain other mutations as well. For example, one or more amino acids of the chemokine can additionally be deleted, substituted or added, the additional mutation can, for example, enhance the inhibitory activity of the mutant cytokine. In a particularly preferred embodiment, the mutant chemokine possesses at least about 85% and preferably at least about 95% homology with the corresponding endogenous chemokine.

In one embodiment, wherein the chemokine is MCP-1, the additional mutation is at the 28-tyrosine and/or 24-arginine, such as the substitution of these amino acids with, for example, aspartate and phenylalanine, respectively.

The mutant chemokines of the present invention are capable of inhibiting one or more activities of the corresponding endogenous chemokine, including binding and/or activating a responsive receptor. By "responsive receptor" it is meant a receptor which is activated by the chemokine. Chemokines have been reported to bind and activate multiple receptors. In a preferred embodiment, the responsive receptor is that which is most highly activated by the chemokine. For example, in the case of MCP-1, the preferred receptor is the MCP-1 receptor.

Figure 1A:
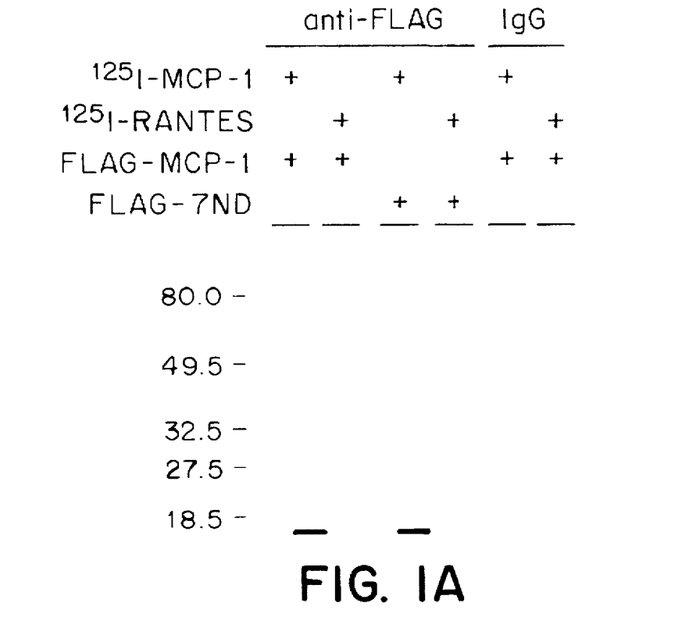
FIG. 1A illustrates a dimerization assay of one ng $^{125}$I-radiolabeled MCP-1 or RANTES (at the same specific activity) mixed with 10 ng non-radiolabeled FX2 (C-terminal FLAG epitope-tagged MCP-1) or 7ND (C-terminal FLAG epitope-tagged mutant MCP-1) as indicated in a total volume of 0.5 ml. Mixtures were subjected to immunoprecipitation using anti-FLAG antibody or murine IgG and analyzed by SDS-PAGE.
Figure 2A:
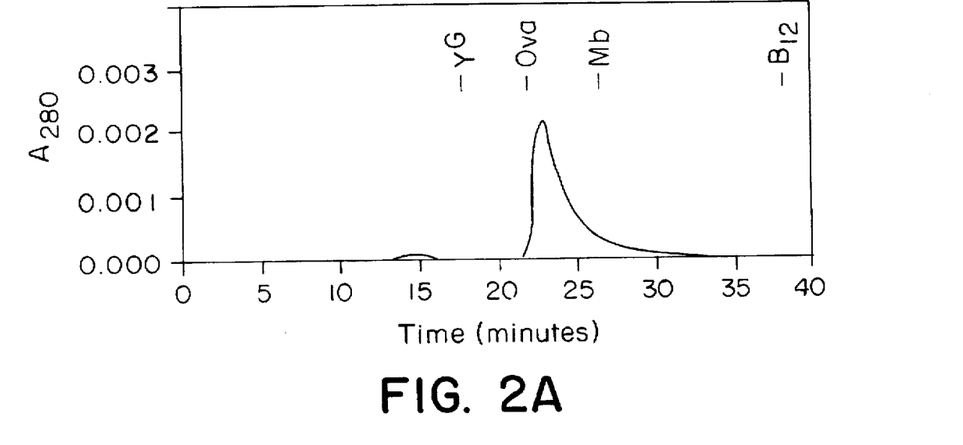
FIGS. 2A, 2B and 2C are illustrations of gel filtration chromatography of MCP-1 variants on Superdex-75. The column was calibrated with standard proteins and $M_r$'s were determined for each species.
Figure 2B:
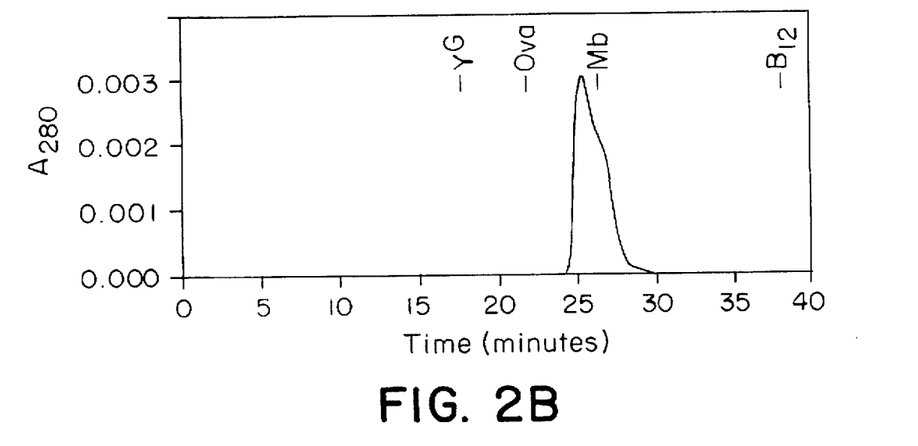

The experimentation described herein indicates that chemokine monomers, such as MCP-1, interact specifically to form homodimers at physiological concentrations. These studies used a C-terminal FLAG epitope-tagged variant of MCP-1 (called FX2) that has full biological activity (Zhang, Y. J. et al., *J. Biol. Chem.* 269:15918–15924 (1994)). When FX2 was mixed with $^{125}$I-MCP-1 at a final chemokine concentration of 2 nM, an anti-FLAG antibody coprecipitated radiolabeled MCP-1 (FIG. 1A). FX2's apparent molecular weight on gel chromatography is 30,600 kD (FIG. 2A), similar to that of unmodified MCP-1 (Rollins, B. J. et al., *Am. J. Pathol.* 136:1229–1233 (1990)), and double its apparent molecular weight on SDS-PAGE (Zhang, Y. J. et al., *J. Biol. Chem.* 269:15918–15924 (1994)). FX2's molecular weight is also double the apparent molecular weight of 7ND, an N-terminal deletion mutant that does not form dimers (see below) and whose predicted molecular weight is only 680 daltons less than monomeric FX2 (FIG. 2B). These observations indicate that MCP-1 forms dimers at physiologically relevant concentrations. Serial immune precipitations showed that approximately 65% of radiolabeled MCP-1 was complexed with FX2 at a concentration of 2 nM.

Figure 1B:
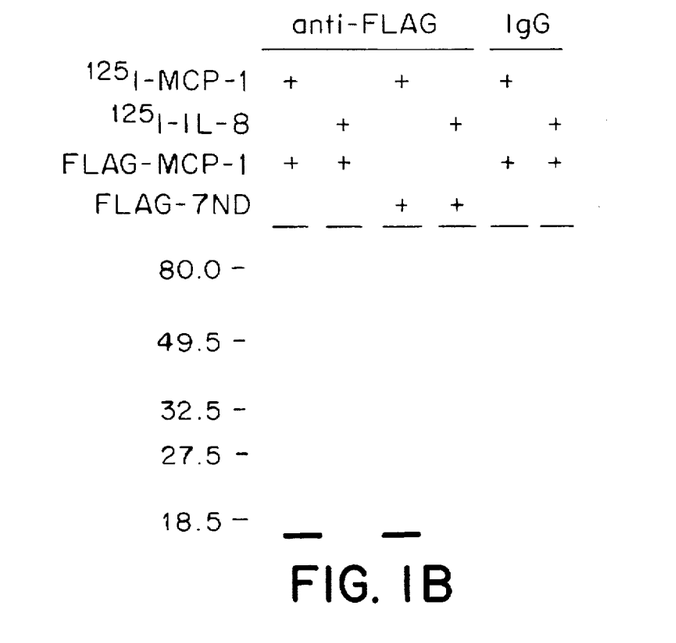
FIG. 1B is the same as 1A except that $^{125}$I-radiolabeled IL-8 was used instead of RANTES, and 600 ng FX2 or 7ND was used.

The specificity of homodimerization was reflected by the fact that FX2 did not form complexes with $^{125}$I-RANTES (a C—C chemokine like MCP-1) or $^{125}$I-IL-8 (a C—X—C chemokine), both radiolabeled to the same specific activity as $^{125}$I-MCP-1. In FIG. 1, no detectable interaction occurred between FX2 and $^{125}$I-RANTES at a physiological chemokine concentration of 2 Nm. In FIG. 1B, we increased FX2's concentration 60-fold. Under these conditions, FX2 still preferentially complexed with $^{125}$I-MCP-1, although a small amount of $^{125}$I-IL-8 co-precipitated with FX2 using anti-FLAG antibody. However, control IgG also precipitated a similar amount of $^{125}$I-IL-8, suggesting that the specificity of homodimerization persisted at concentrations as high as 120 nM.

Figure 3:
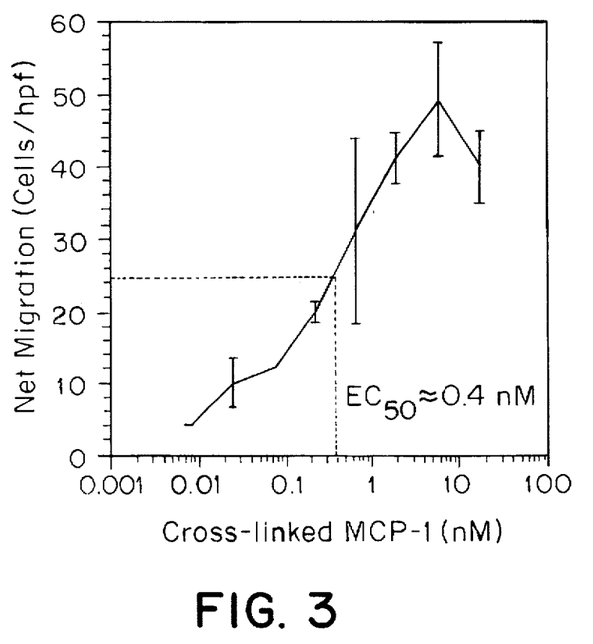

Having determined that MCP-1 forms dimers, MCP-1 dimers were demonstrated to be biologically active by using the bifunctional crosslinker disuccinimidyl suberate (DSS) to construct stably dimerized molecules. FIG. 3 shows an example of a crosslinked MCP-1 preparation in which the relative contributions of monomeric and multimeric species, as determined by laser densitometry, were 3% monomers, 63% dimers, 21% trimers, and 13% tetrameres. Independent crosslinking experiments performed under the same conditions routinely produced similar product distributions. This material was tested for monocyte chemoattractant activity, and using a molecular weight based on the abundance of each species, its EC$_{50}$ was approximately 400 pM, the same as the specific activity of non-crosslinked MCP-1. (Matsushima, K. et al., *J. Exp. Med.* 169:1485–1490 (1989); Yashimura, T. et al., *J. Exp. Med.* 169:1449–1459 (1989)).

The data of FIG. 3 indicate that multimers of MCP-1, including dimers, are fully active as chemoattractants, but they do not show that dimerization is necessary for activity. To demonstrate this, an MCP-1 variant was used which lacks amino acids 2–8 of the processed protein. This variant, called 7ND, is a potent and specific inhibitor of monocyte chemotaxis in response to MCP-1.

Figure 4:
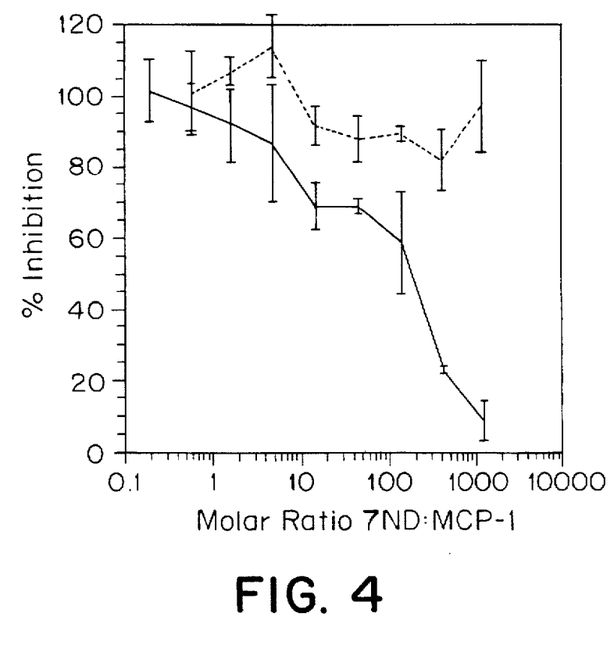
FIG. 4 shows increasing amounts of purified 7ND added to constant amounts of uncrosslinked MCP-1 (10 ng/ml; 0.9 nM; solid line) or crosslinked MCP-1 (19 ng/ml; 0.7 nM; dotted line). The mixtures were then tested for their ability to attract monocytes in vitro relative to their chemoattractant activity in the absence of 7ND. Error bars indicate the standard error of measurements in duplicate wells; this experiment is representative of three.

Two experiments indicated that 7ND is a dominant negative. First, 7ND specifically forms heterodimers with wild-type MCP-1. FIG. 1 shows that anti-FLAG antibodies co-precipitated radiolabeled MCP-1 (but not RANTES or IL-8) along with 7ND, which contains the FLAG epitope. Second, 7ND could inhibit wild-type MCP-1 activity by two possible mechanisms: either it is a competitive inhibitor for receptor binding, or it is a dominant negative. The crosslinked dimer was used to distinguish between these possibilities. FIG. 4 shows that 7ND inhibited monocyte chemotaxis in response to non-crosslinked MCP-1, but had no effect on crosslinked MCP-1. This indicates that 7ND exerts its effects as a dominant negative, and further suggests that the biologically active form of MCP-1 is a dimer.

Finally, the need for dimerization was demonstrated in a different way by examining an inactive MCP-1 variant in which the FLAG epitope was inserted immediately after the N-terminal glutamine. Although this variant appears to form homodimers by the criteria of its size on gel filtration chromatography (FIG. 2C) and its ability to coprecipitate with MCP-1 (data now shown), it has only 0.2% of wild-type chemoattractant activity (Zhang, Y. J. et al., *J. Biol. Chem.* 269:15918–15924 (1994)). However, because it has a full-length N-terminus, DSS can crosslink these homodimers, and crosslinking restores its ability to attract monocytes. Thus, physically constraining the altered N-termini of N-terminal FLAG MCP-1 dimers produces monocyte chemoattractant activity, again indicating that dimeric MCP-1 activates its receptor.

Using co-precipitation, MCP-1 has been demonstrated to specifically form homodimers at physiological concentrations. Dimeric MCP-1 is fully active as a monocyte chemoattractant because the specific activity of chemically crosslinked MCP-1 was indistinguishable from non-crosslinked MCP-1. The need for dimerization was examined by using 7ND, an N-terminal deletion mutant of MCP-1 that inhibits the monocyte chemoattractant activity of non-crosslinked MCP-1. However, 7ND's inability to inhibit monocyte chemotaxis in response to crosslinked MCP-1 supports the conclusion that 7ND acts as a dominant negative mutant of MCP-1 which means, in turn, that MCP-1 must activate its receptor as a dimer. Finally, supportive evidence for dimerization came from the observation that crosslinking an inactive N-terminal FLAG insertional mutant restores its activity.

Taken together the results suggest a model in which dimeric MCP-1 binds to its receptor. The N-terminus and one face of the first predicted β sheet are essential for MCP-1's chemoattractant activity. Without being limited to a particular mechanism of action, these observations can be combined with our current results in three different models. First, mutating the N-terminus and first β sheet can destroy activity simply by preventing dimerization, and dimerization per se can be essential for activity because apposing non-contiguous regions of the proteins (not at the N-terminus) creates the active ligand. However, this model would not explain why 7ND/MCP-1 heterodimers are inactive. Alternatively, the N-terminus and first β sheet may be essential because they interact directly with the receptor, and dimerization is necessary because two of these areas must bind to one receptor in order to generate a signal. This would explain restoration of crosslinked N-terminal FLAG-MCP-1's activity by forcing its dimerization. The N-terminal insertion would prevent two N-termini from interacting with the receptor due to steric hindrance or charge repulsion (the FLAG epitope is essentially a polyanion of aspartic acids). Crosslinking, which occurs at the N-termini, would then constrain the N-termini to fit into their binding region in the receptor. This model would also explain 7ND's dominant negative activity: 7ND/MCP-1 heterodimers could dock in the receptor but could not activate it because one of the two required N-termini would be missing. There is precedent for peptide ligands that interact with 7-TMS receptors at multiple sites (Siciliano, S. J. et al., *Proc. Natl. Acad. Sci. USA* 91:1214–1218 (1994)). In a third model, MCP-1 dimers might bring two receptors together for their activation, by analogy to tyrosine kinase receptors. Our data are consistent with this model, but there is no evidence yet to support 7-TMS receptor interaction.

Direct measurements of MCP-1 monomer-dimer equilibria suggest that the dissociation constant for the dimer is several logs above MCP-1's $EC_{50}$ (Paolini, J. F. et al., *J. Immunol.* 153:2704–2717 (1994)). These observations do not contradict the findings disclosed herein. First, the equilibrium in solution may not reflect the equilibrium at the receptor, since the binding site for MCP-1 may have a conformation that greatly favors dimerization. Second, local concentrations of MCP-1 may be influenced by other molecules at the cell surface. For example, chemokines interact with glycosaminoglycans which cover the surface of monocytes and endothelial cells (Webb, L. M. C. et al., *Proc. Natl. Acad. Sci. USA* 90:7158–7162 (1993)). As chemokines are added to monocytes in vitro or as they appear at the endothelial cell surface in vivo, their binding to glycosaminoglycans could create extremely high local concentrations that might exceed the $K_d$ for dimerization, thereby providing a mechanism for the modulation of their leukocyte chemoattractant activity. Thus, where the $K_d$ for MCP-1 dimerization is higher than the $K_d$ for receptor binding, then the appearance of active MCP-1 depends on achieving high local concentrations. This effectively changes the shape of the chemoattractant gradient to one that is much steeper near its source and falls off more rapidly with distance than it otherwise would. "Self-inactivation" would then occur rapidly with increasing distance from the secreting cell. The extremely steep gradient may prevent aberrant leukocyte migration, and may enable cells to be precisely directed over extremely short distances, providing greater control and specificity for leukocyte trafficking. This mechanism also identifies a new drug target for inhibiting chemokine activity, namely the dimer interface.

Finally, the published $K_d$ for monomer dissociation may be incorrect. The published values were derived using equilibrium sedimentation centrifugation, gel filtration chromatography, and chemical crosslinking. All of these techniques are somewhat indirect. The monomer affinities were measured directly herein by biospecific interaction analysis (BiAcore™ from Pharmacia Biotechnology, Inc.) and found that the $K_d$ for monomer dissociation in MCP-1 homodimers is 84 pM. This value, determined by direct real-time observation, indicates that at physiological concentrations, most MCP-1 will be present as dimers, and places the application of dominant negative inhibition, already established empirically, on firm theoretical grounds.

Thus, the invention further relates to the use of mutant chemokines which inhibit the activity of the endogenous or corresponding cytokine in vivo or in vitro.

For example, the mutant chemokine can be added in a sample (such as a blood sample) to be subjected to an assay to selectively inhibit a targeted chemokine. In such a method, the assay can accurately measure the chemoattractant or other activity of the targeted or different chemokine. Thus, the mutant chemokine can be added to assays such as those described in Falk et al., *J. Immunol. Methods* 33:239–247 (1980) or in Westwick, J. "Cytokines, a practical approach," F. R. Balkwill, ed., 1991, IRL Press, Oxford, pp. 197–204.

In a particularly preferred embodiment, the mutant chemokine is administered to a mammal, such as an individual or a patient, for the treatment of a chemokine mediated disease, such as inflammation, auto-immune disease and coronary artery restenosis.

Chemokines are implicated in the attracting leukocytes, such as monocytes, to damaged coronary arteries, such as the damage caused by coronary artery angioplasty, and are involved in causing restenosis. Administration of inhibitors to the recruitment of leukocytes will be useful in preventing coronary artery restenosis, autoimmune diseases, such as rheumatoid arthritis, inflammatory bowel disease and multiple sclerosis, chronic pulmonary inflammation, such as pulmonary fibrosis, and other conditions linked to the recruitment of leukocytes, such as monocytes.

The derivatives of the claimed invention can be administered alone or in a suitable pharmaceutical composition. Modes of administration are those generally known in the art, such as parenteral application and the administration of a recombinant host cell, DNA or infectious vector which, upon administration, will express the protein in vivo. See, e.g. U.S. Pat. No. 5,399,346 to Anderson et. al., which is incorporated herein by reference.

Suitable pharmaceutical carriers include, but are not limited to water, salt solutions, alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, and/or aromatic substances and the like which do not deleteriously react with the active compounds. They can also be combined where desired with other active agents, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampoules are convenient unit dosages.

It will be appreciated that the actual amounts of the MCP-1 derivative in a specific case will vary according to the specific compound being utilized, the particular composition formulated, the mode of administration and the age, weight and condition of the patient, for example. Dosages for a particular patient can be determined by one of ordinary skill in the art using conventional considerations, (e.g. by means of an appropriate, conventional pharmacological protocol).

The invention also relates to the isolated DNA, encoding the mutant chemokine described herein, vectors and recombinant host cells containing the same.

The isolated DNA can be the endogenous genomic or cDNA encoding the chemokine, deleting the codons corresponding to the amino acids deleted in the mutant chemokine. Also envisioned are silent mutations thereof (wherein one or more base pairs are modified, substituted or mutated such that the encoded protein sequence is the same). In a particularly preferred embodiment, the isolated DNA can hybridize to, preferably under stringent conditions, the corresponding genomic or cDNA molecule encoding the endogenous chemokine. In a more preferred embodiment, the isolated DNA is at least about 85% or, more preferably, at least about 95%, homologous to the corresponding genomic or cDNA sequence.

As stated above, the invention further relates to vectors containing the isolated DNA. Such vectors include infections (such as retroviral, adenoviral and vaccinia vectors, for example) and non-infections vectors, the vectors of the claimed invention can be readily prepared employing known techniques (such as, Ausubel et al. *Current Protocols in Molecular Biology*, Greene Publishing Assoc. and Wiley-Interscience (1989) and Sambrook et al., *Molec. Cloning*, Cold Spring Harbor Press (1989)) from commercially available starting materials.

The vectors generally contain a suitable promoter (such as, a constitutive or inducible promoter recognized by the recipient host cell) and, optionally, a selectable marker, such that, upon insertion of the DNA into the host cell, the cell can express and, preferably, secrete the mutant chemokine. Promoters and selectable markers are well known in the art and can, generally, be obtained commercially. In a preferred embodiment, the promoter is the endogenous chemokine promoter.

These vectors can be used directly for the administration to an individual for in vivo expression of a therapeutically effective amount of the mutant chemokine or can be used to deliver the isolated DNA to a host cell in vitro.

In the latter embodiment, the cell can be transfected (e.g., by calcium phosphate precipitation, electroporation or microinjection) or infected (e.g., by retroviral, adenoviral or vaccinia infection) employing well known techniques in the art, as described in the references cited above. Suitable host cells include commercially available cells, e.g., mammalian cell lines, such as Chinese hamster ovary cells (CHO cells) and human cell lines or TIL cells.

The recombinant cells of the present invention thus made include the recombinant DNA encoding the mutant chemokine under the control of a suitable promoter and, preferably, a selectable marker. The recombinant cells thus obtained can then be selected, cloned and/or cultured in vitro and/or administered to the individual for in vivo protein expression, as described above. In one embodiment, the recombinant host cells are cultured in vitro, thereby expressing and secreting the mutant chemokine which can then be purified to the desired degree by methods generally known in the art.

The invention is further specifically illustrated by the following examples.

EXEMPLIFICATION

Construction and Expression of Epitope-Tagged MCP-1 and Wild-Type MCP-1

Starting with pGEM-hJE34 (human MCP-1 cDNA in pGEM-7 (Promega, Wis.)) as a template, recombinant PCR was used to insert 30 nucleotides immediately 5' to the termination codon (position 366) encoding the FLAG epitope (Prickett, (1989)) with a two glycine spacer. Sequence analysis of the resulting cDNA revealed no other base alterations, and the entire cDNA was cloned into the expression vector pmt21 (Genetics Institute) to yield a plasmid designated pFX2.

COS cells were suspended in serum-free Dulbecco's modified Eagle's medium (DMEM) at $5 \times 10^6$ cells/ml. Four$\times 10^6$ cells (0.8 ml) were placed in an electroporation cuvette with a 0.4 cm gap, 10 µg plasmid DNA was added, and the cells were electroporated at 0.28 kV, 960 µF (yielding a time constant of 10–13 msec). Cells were allowed to recover in the cuvette at room temperature for 10 minutes, then plated in two 100 mm dishes in DMEM with 10% bovine calf serum. After 24 hours, medium was changed to serum-free DMEM. After an additional 24 hours, conditioned medium was collected, cells and debris were removed by centrifugation, and the medium was stored at −70° C.

Wild-type MCP-1 was also produced by COS cell transfection, as described above, and obtained from Genzyme Corp. (Boston, Mass.).

Construction and Expression of MCP-1 Mutations

Similar techniques as described above were used to insert the FLAG epitope and spacer immediately 3' to the codon for aspartate-3 in processed MCP-1 (nucleotide position 146); this expression plasmid was designated pFX3. Based on modeling considerations as well as structure/activity data from other chemokines (in particular IL-8), MCP-1 mutations in three regions were constructed: namely the N-terminus, the first inter-cysteine loop, and the C-terminal predicted α-helix (FIGS. 2 and 4). With pFX2 as template, recombinant PCR was used to insert, termination codons or single amino acid changes. All mutations were confirmed by sequence analysis of both DNA strands.

$^{125}$I-radiolabeled MCP-1, IL-8, and RANTES were purchased from NEN/DuPont (Boston, Mass.) and all had specific activities of 2200 Ci/mmol. FX2 (C-terminal epitope-tagged MCP-1), an N-terminal epitope-tagged MCP-1, and 7ND (N-terminal MCP-1 deletion mutant) were prepared by expression of their cDNA's in Chinese hamster ovary cells (Rollins, B. J. and Sunday, M. E., *Mol. Cell. Biol.* 11:3125–3131 (1991) or *E. coli* (Zhang, Y. J. et al., *J. Biol. Chem.* 269:15918–15924 (1994)) and were purified by FLAG affinity purification as described (Zhang, Y. J. et al., *J. Biol. Chem.* 269:15918–15924 (1994)).

Immunoblotting

Conditioned medium from transfected COS cells was boiled in sample buffer and subjected to electrophoresis through a 15% polyacrylamide gel in SDS. In some cases, medium was first concentrated using a Centricon-10 device (Amicon, Danvers, Mass.).

Proteins were electrophoretically transferred to nitrocellulose and probed either with an anti-FLAG M1 monoclonal antibody (International Biotechnologies, Inc., New Haven, Conn.) or with rabbit anti-MCP-1 antiserum.

Blots were developed using the appropriate horseradish peroxidase-conjugated secondary antibody and substrate solution Vector Laboratories, Burlingame, Calif.).

Quantitation of MCP-1 and its Derivatives

MCP-1 was expressed as a FLAG fusion protein in *E. coli* using the FLAG Biosystem and purified using an anti-FLAG affinity column (International Biotechnologies, Inc., New Haven, Conn.). Known amounts of pure FLAG-MCP-1 fusion protein were included in every immunoblot for MCP-1 produced by COS cells. Immunoblots were then analyzed by laser densitometry (Pharmacia, Piscataway, N.J.) and the mass of each COS cell-produced protein was determined by reference to the FLAG-MCP-1 fusion standard. The amount of COS cell supernatant loaded in each well generated an immunoblot signal within the linear response range of the laser densitometer. When possible, samples were quantitated using both anti-FLAG and anti-MCP-1 antibodies. There were no disparities between amounts of protein determined with the two antibodies except when one of the epitopes was absent.

Monocyte Chemotaxis Assay

Human peripheral blood mononuclear cells were prepared from volunteers as described (Rollins, Blood, 78, pp. 1112–1116 (1989)). Chemotaxis assays were performed using a multiwell chamber fitted with a polycarbonate filter having 5 μ pores as described. Each COS cell supernatant was tested over a wide range of dilutions, and the concentration of monocyte chemoattractant activity (MCA) in each supernatant was defined as the inverse of the dilution giving half-maximal chemotactic response.

Figure 6:
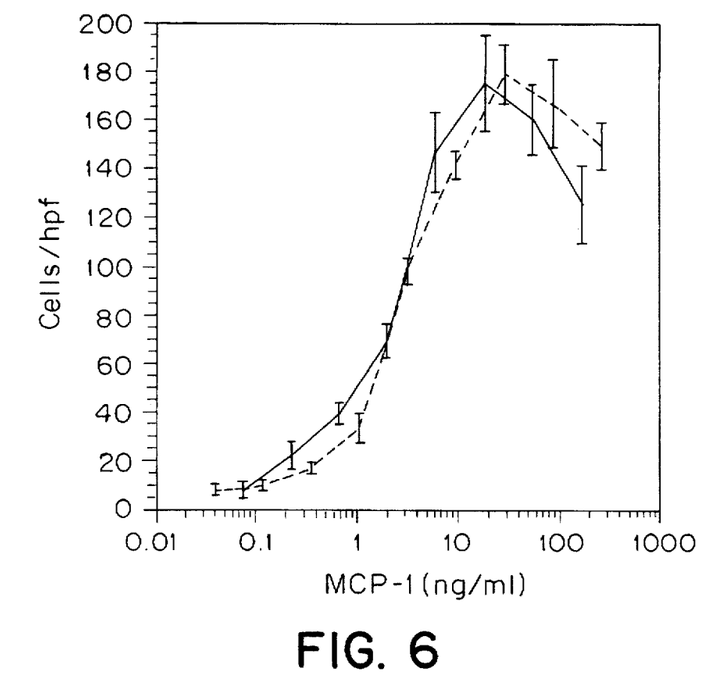
FIG. 6 is a response curve of wild type MCP-1 and FLAG epitope tagged MCP-1 proteins.

Wild-type MCP-1 and FX2 had similar dose response characteristics, FIG. 6. Using the quantitation results from immunoblotting, analysis of the dose response curves showed that the specific activity of FX2 is 408,000 U/ml while that of wild-type MCP-1 is 442,000 U/ml. Both values compared favorably with the specific activity determined for purified, eukaryotically-produced, recombinant MCP-1, suggesting that the epitope tag does not interfere with MCP-1's ability to attract monocytes in vivo.

Figure 7:
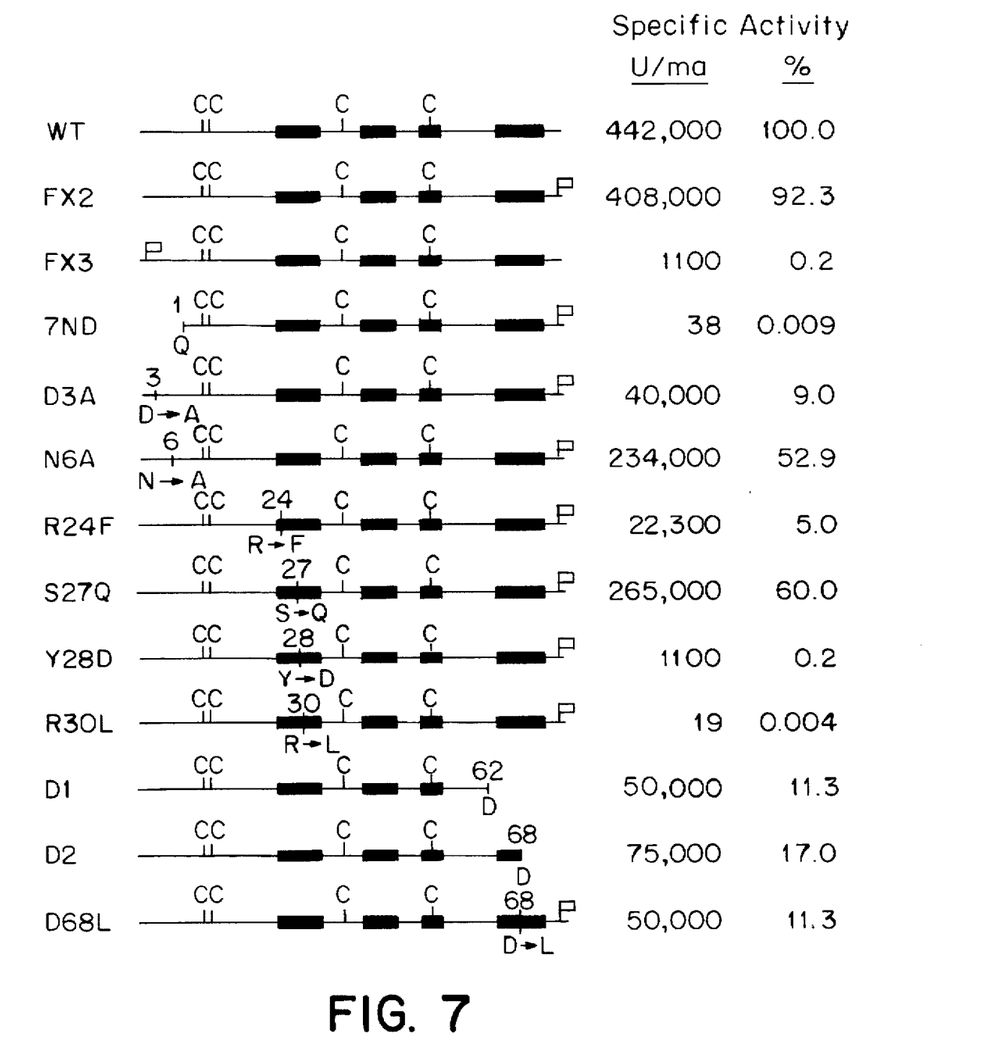
FIG. 7 is a chart of the mutations prepared and the specific chemotaxis activity of the mutants.

Each of the mutations constructed, illustrated in FIG. 7, were tested for monocyte chemotaxis activity in the same manner. As set forth above, the mutations were constructed in three regions, the N-terminus, the first inter-cysteine loop, and the C-terminus. At the N-terminus, insertion of the FLAG epitope immediately after the N-terminal glutamine destroyed the protein's monocyte chemoattractant activity (FX3). Consistent with that finding was the fact that deletion of amino acids 2–8 also yielded an inactive protein. In an attempt to accomplish finer mapping, the two charged amino acids were changed in this region (aspartate-3 and asparagine-6) to alanine. Changing aspartate-3 significantly reduced the activity of the protein, while changing asparagine-6 yielded a protein that retained 52.9% of wild-type MCP-1's activity.

Next, four point mutations in the first intercysteine loop were constructed. Mutations of arginine-24 to phenylalanine, tyrosine-28 to aspartate, and arginine-30 to leucine all produced proteins with activities that were only a fraction of wild-type. However, mutation of another polar amino acid in the same region, namely serine-27, produced a protein with 60% of the activity of wild-type.

Finally, manipulations of the C-terminal α-helix produced proteins that were still able to signal, but had reduced potency compared to wild-type. Deletions of half (D2) or all (D1) of the α-helix yielded proteins with 17% and 11.3% of wild-type activity, respectively. In the predicted model structure of dimeric MCP-1, aspartate-68 projects into a predicted receptor binding cleft between two α-helices. Mutation of this amino acid to leucine had the same effect as deletion of the entire helix.

Competition for Biological Effects

Figure 8:
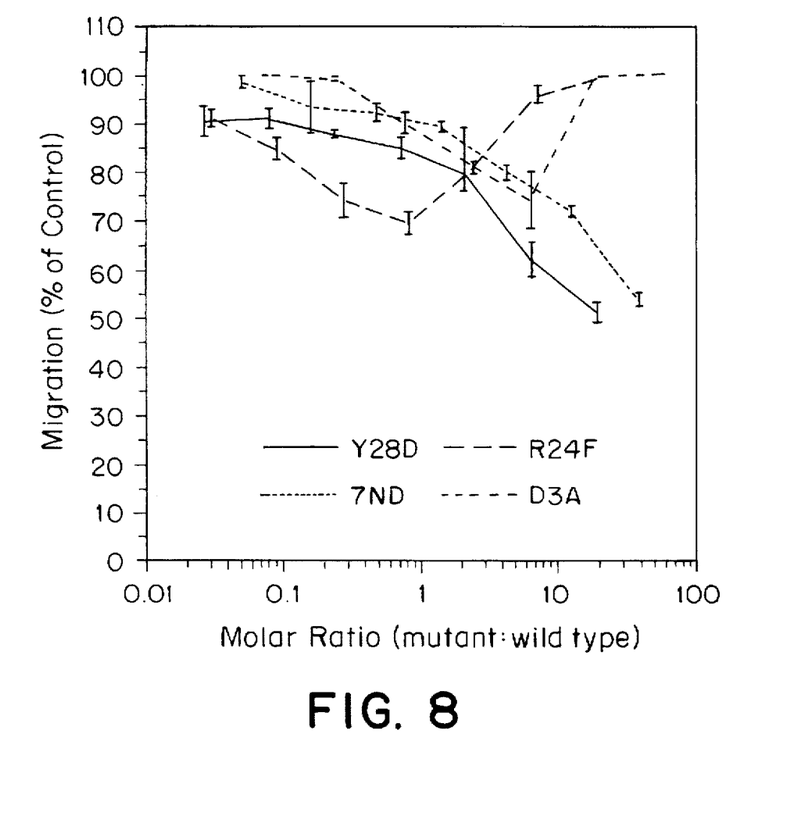
FIG. 8 is a dose response curve for MCP-1 inhibition of four MCP-1 inhibitors.

Mutated MCP-1 derivatives were tested for their ability to inhibit monocyte chemotaxis in vitro in response to non-mutated MCP-1. To a fixed concentration of FX2, increasing amounts of medium conditioned by COS cells expressing mutant proteins were added. Only Y28D, R24F, 7ND, and D3A demonstrated an ability to inhibit wild type MCP-1. FIG. 8 shows that Y28D and 7ND were able to inhibit monocyte chemotaxis to FX2 by approximately 50% at the highest ratios tested. (The upper limit was dictated by the concentration of mutation protein in conditioned medium.) Y28D was slightly more effective than 7ND on a molar basis with an ID$_{50}$ corresponding to ≈300 ng/ml in the presence of 10 ng/ml wild-type MCP-1. R24F reduced MCP-1's chemoattractant effect to 69% of control at a molar ratio of 1:1. Although R24F itself had monocyte chemoattractant activity of only 5% of wild-type, addition of more R24F beyond a 1:1 molar ratio with wild-type led to increasing chemoattractant activity. D3A reduced MCP-1's activity to 80% of control at a molar ratio of 10:1, but since it also has chemoattractant activity, higher molar ratios showed loss of inhibition. Inhibitory activity was specific for MCP-1 since the mutations did not inhibit monocyte chemotaxis in response to formyl-methionyl-leucyl-phenylalanine (fMLP).

Figure 9:
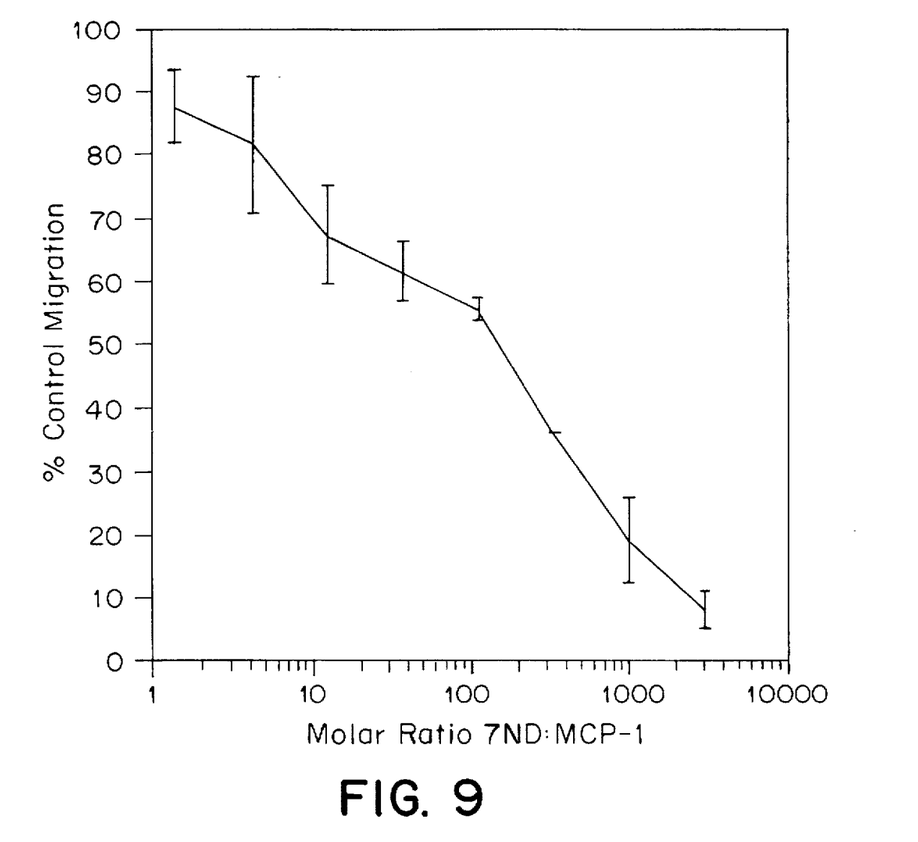
FIG. 9 illustrates the inhibition of 7ND on MCP-1 monocyte chemotaxis.

7ND was purified and added to a constant amount of wild-type MCP-1. FIG. 9 shows that 7ND could completely inhibit monocyte chemotaxis in response to 5 mg/ml wild-type MCp-1 with an $IC_{50}$ that occurred at a molar ratio of 75:1. Thus the N-terminal deletion mutant, 7ND, can fully inhibit the chemoattractant activity of MCP-1.

Immune Precipitations $^{125}$I-radiolabeled chemokines were mixed with epitope-tagged chemokines in PBSA and incubated at 4° C. for 1 hour, then 10 µg anti-FLAG M2 antibody (International Biotechnologies, Inc., New Haven, Conn.) or murine IgG (Sigma, St. Louis, Mo.) were added. The mixture was incubated at 4° C. for 1 hour with gentle rotation, after which 50 µl of staphylococcal protein A beads (BioRad, Richmond, Calif.) was added and the incubation continued for an additional hour. Beads were collected by centrifugation, then washed twice with RIPA buffer (50 mM Tris hydrochloride [pH 7.5], 150 mM NaCl, 0.1% SDS, 1% Triton X-100, 0.5% deoxycholate, 1 mM phenylmethylsulfonyl fluoride) and twice with 50 mM Tris hydrochloride (pH 7.5), 1M NaCl. Beads were resuspended in sample buffer containing SDS and β-mercaptoethanol, and then boiled. Released proteins were fractionated by SDS-PAGE through 15% polyacrylamide, and dried gels were analyzed by autoradiography. The results are shown in FIGS. 1A and 1B.

Gel Filtration Chromatography

Figure 2C:
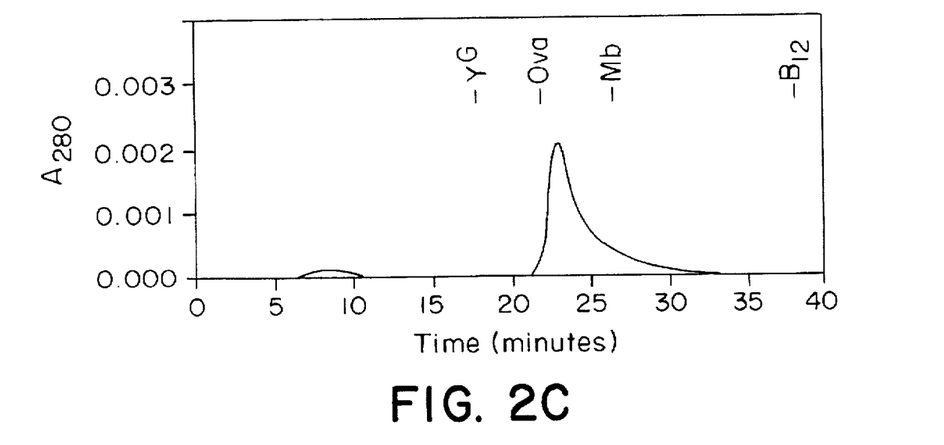

Seven to 9 µg of MCP-1 or its derivatives were loaded on a 25 ml Superdex-75 column (Pharmacia, Piscataway, N.J.) which was developed in 50 mM sodium phosphate (pH 7.4), 150 mM NaCl at a flow rate of 0.5 ml/min. The column was calibrated in the same buffer using standards obtained from BioRad (Richmond, Cailf.). The results are shown in FIGS. 2A, 2B and 2C.

Crosslinking

Five µg of chemokine was resuspended in 445 µl PBS at 4° C. and 5 µl of a 20 mM solution of DSS$^1$ (Pierce, Rockford, Ill.) was added. The mixture was incubated at 4° C. for 45 minutes, then concentrated and cleared of crosslinker by centrifugation using a Centricoh-10 device (Amicon, Danvers, Mass.). Crosslinked products were fractionated by SDS-PAGE on 15% polyacrylamide gels. After silver staining, the proportion of monomers and multimeric species was determined by laser densitometry (Pharmacia, Piscataway, N.J.).

Monocyte Chemoattraction Assays

Figure 5:
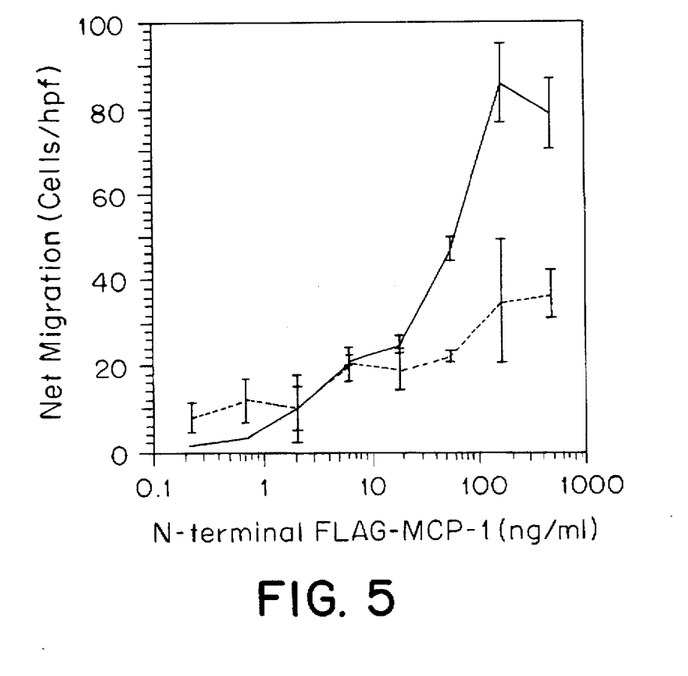
FIG. 5 is a non-crosslinked (dotted line) and crosslinked (solid line) N-terminal FLAG-MCP-1 tested in monocyte chemoattraction assays. Error bars indicate the standard error of measurements in duplicate wells; this experiment is representative of two.

Monocyte chemoattraction assays were performed on human peripheral blood mononuclear cells using a multi-well modified Boyden chamber device as described above. The results are set forth in FIGS. 3, 4, and 5.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A mutant chemokine comprising an N-terminal deletion mutation of the endogenous chemokine, wherein said mutant chemokine is without chemokine activity and inhibits endogenous chemokine binding and activation of a responsive chemokine receptor, with the proviso that the chemokine is not interleukin-8.

2. The mutant chemokine of claim 1 comprising an N-terminal deletion of a C—C chemokine.

3. The mutant chemokine of claim 1 comprising an N-terminal deletion of a C—X—C chemokine.

4. The mutant chemokine of claim 1 wherein the N-terminal β-sheet is deleted.

5. The mutant chemokine of claim 1 wherein amino acids between about 1 to about 13 of the endogenous chemokine are deleted.

6. The mutant chemokine of claim 5 wherein amino acids between about 1 to about 10 of the endogenous chemokine are deleted.

7. The mutant chemokine of claim 6 wherein amino acids between about 2 to about 7 of the endogenous chemokine are deleted.

8. The mutant chemokine of claim 1 comprising an N-terminal deletion of a chemokine selected from the group consisting of MCP-1, MCP-2, MCP-3, MIP-1α, MIP-1β, RANTES, platelet factor 4, IP-10, GROα, GROβ, GROγ, NAP-2, ENA-78, CTAP-III, MIG and I-309.

9. A chemokine heterodimer comprising a monomeric N-terminal deletion mutation of the endogenous chemokine and a monomeric unit of the endogenous chemokine, wherein said monomeric N-terminal deletion mutation inhibits binding of the endogenous chemokine to its receptor, with the proviso that the chemokine is not interleukin-8.

10. A method for treating a chemokine-mediated disease comprising administering to a patient in need thereof a mutant chemokine comprising an N-terminal deletion mutation of the endogenous chemokine, wherein said mutant chemokine is without chemokine activity and inhibits binding of the endogenous chemokine to its receptor responsive thereto, with the proviso that the chemokine is not interleukin-8.

11. The method of claim 10 wherein the mutant chemokine comprises an N-terminal deletion of a C—C chemokine.

12. The method of claim 10 wherein the mutant chemokine comprises an N-terminal deletion of a C—X—C chemokine.

13. The method of claim 10 wherein the mutant chemokine comprises an N-terminal β-sheet is deleted in the endogenous chemokine.

14. The method of claim 10 wherein the mutant chemokine comprises a deletion of amino acids between about 1 to about 13 of the endogenous chemokine.

15. The method of claim 14 wherein the mutant chemokine comprises a deletion of amino acids between about 1 to about 10 of the endogenous chemokine.

16. The method of claim 15 wherein the mutant chemokine comprises a deletion of amino acids between about 2 to about 7 of the endogenous chemokine.

17. The method of claim 10 wherein the mutant chemokine comprises an N-terminal deletion of a chemokine selected from the group consisting of MCP-1, MCP-2, MCP3, MIP-1α, MIP-1β, RANTES, platelet factor 4, IP-10, GROα, GROβ, GROγ, NAP-2, ENA-78, CTAP-III, MIG and I-309.

18. The method of claim 17 wherein the chemokine-mediated disease is selected from the group consisting of: atherosclerosis, coronary artery restenosis, autoimmune disease, rheumatoid arthritis, asthma, inflammatory bowel disease, pulmonary fibrosis and multiple sclerosis.

19. A method for the production of a mutant chemokine comprising maintaining a recombinant cell which expresses the mutant chemokine under conditions which result in the expression of the mutant chemokine; wherein the mutant chemokine comprises an N-terminal deletion mutation of the endogenous chemokine which is without chemokine activity and inhibits endogenous chemokine binding and activation of a responsive chemokine receptor, with the proviso that the chemokine is not interleukin-8.

20. The method of claim 19 further comprising the step of isolating the mutant chemokine.

21. The method of claim 19 wherein the mutant chemokine is secreted from the recombinant cell.

* * * * *